United States Patent [19]

Maekawa

[11] Patent Number: 5,434,081
[45] Date of Patent: Jul. 18, 1995

[54] METHOD OF CLASSIFYING LEUKOCYTES BY FLOW CYTOMETRY

[76] Inventor: Yasunori Maekawa, 35-111, Asahigaoka, Bessho-cho, Miki-shi, Hyogo-ken, Japan

[21] Appl. No.: 131,016

[22] Filed: Oct. 1, 1993

Related U.S. Application Data

[63] Continuation of Ser. No. 790,415, Nov. 7, 1991, abandoned.

[30] Foreign Application Priority Data

Nov. 16, 1990 [JP] Japan .................................. 2-310730

[51] Int. Cl.⁶ .............................................. G01N 1/30
[52] U.S. Cl. .................................. 436/17; 436/166; 436/172; 436/174; 436/800; 436/805
[58] Field of Search ................ 436/63, 166, 172, 174, 436/17, 800, 805, 519; 424/11; 435/7.24, 29

[56] References Cited

U.S. PATENT DOCUMENTS

| | | | |
|---|---|---|---|
| 4,027,971 | 6/1977 | Kolman et al. | 356/26 |
| 4,345,027 | 8/1982 | Dolbeare | 435/21 |
| 4,628,026 | 12/1986 | Gardell et al. | 435/7 |
| 4,637,986 | 1/1987 | Brown et al. | 436/10 |
| 4,656,139 | 4/1987 | Matsuda et al. | 438/17 |
| 4,727,020 | 2/1988 | Recktenwald | 435/6 |
| 4,751,179 | 6/1988 | Ledis et al. | 436/34 |
| 4,812,394 | 3/1989 | Dolbeare et al. | 435/6 |
| 4,902,613 | 2/1990 | Chang et al. | 435/2 |
| 4,959,301 | 9/1990 | Weaver et al. | 435/5 |
| 4,968,629 | 11/1990 | Lapicola | 436/18 |
| 4,978,624 | 12/1990 | Cremins et al. | 436/17 |
| 5,039,613 | 8/1991 | Matsuda et al. | 436/17 |
| 5,057,413 | 10/1991 | Terstappen et al. | 435/6 |
| 5,084,378 | 1/1992 | Crissman et al. | 435/6 |
| 5,175,109 | 12/1992 | Sakata et al. | 436/17 |

OTHER PUBLICATIONS

Floy J. Green, The Sigma-Aldrich Handbook of Stains, Dyes and indicators, 1990, p. 318 and Transmisasion Spectrum Reference chart.

*Primary Examiner*—James C. Housel
*Assistant Examiner*—Long V. Le

[57] ABSTRACT

A method for leukocyte classification by flow cytometry that uses a first fluid that is hypotonic acidic fluorescent dye solution and a second fluid that is a solution that changes the osmolarity and pH of the first fluid is disclosed. The first fluid to be used in the method incorporates not only the first and second dyes but also the third dye and this insures that even leukocytes with damaged cell membrane can be distributed as entities distinct from other leukocyte types on a two-dimensional plot. And, hence, high precision of leukocyte classification is assured even in the case of assaying blood that contains damaged cells as a result of prolonged standing at room temperature after sampling.

11 Claims, 7 Drawing Sheets

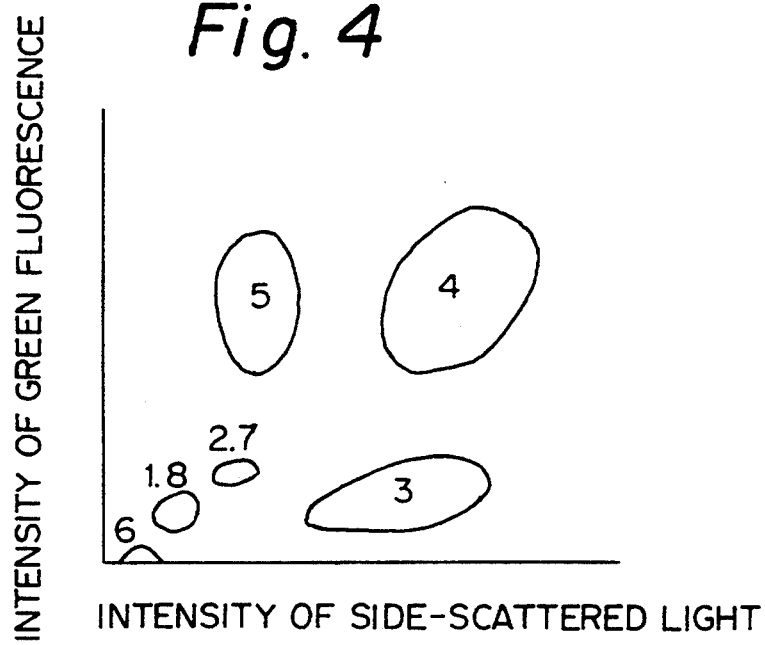
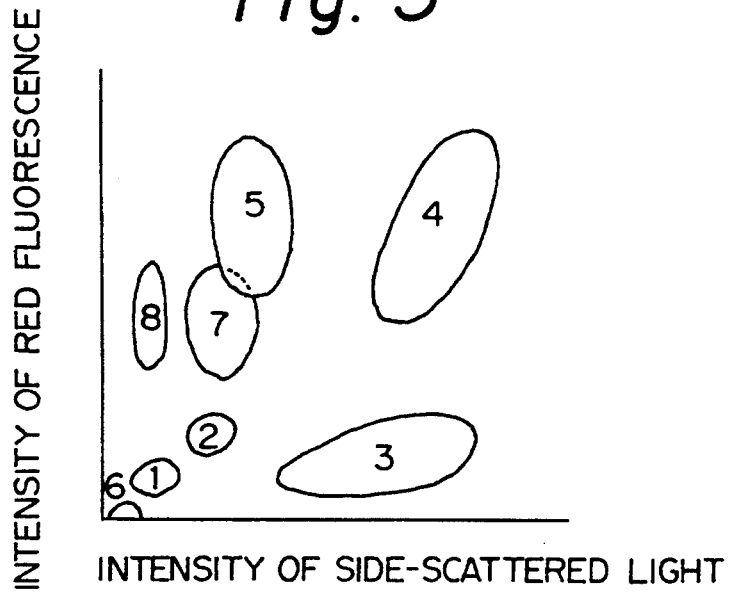

INTENSITY OF SIDE-SCATTERED LIGHT

INTENSITY OF SIDE-SCATTERED LIGHT

INTENSITY OF GREEN FLUORESCENCE

INTENSITY OF SIDE-SCATTERED LIGHT

INTENSITY OF RED FLUORESCENCE

INTENSITY OF SIDE-SCATTERED LIGHT

METHOD OF CLASSIFYING LEUKOCYTES BY FLOW CYTOMETRY

This is a continuation of application Ser. No. 07/790,415, filed Nov. 7, 1991, now abandoned.

BACKGROUND OF THE INVENTION

1. Field of the Invention

This invention relates to a method for classifying leukocytes in the practice of clinical testing. More particularly, this invention relates to a method of classifying leukocytes with a flow cytometer by means of optical measurements on blood cells stained with fluorescent dyes, which method is capable of maintaining the desired precision of leukocyte classification irrespective of the difference in the lapse of time following blood sampling.

2. Prior Art

Leukocytes in the peripheral blood of normal subjects can be classified as being of five types consisting of lymphocytes, monocytes, neutrophils, eosinophils, and basophils. Different leukocyte types have different functions and counting of leukocytes in the blood according to their type provides valuable information for diagnostic purposes. For instance, an increase in the number of neutrophils is-associated with inflammation, and diseases such as myocardial infarction and leukemia, and a decrease in their number is associated with vital diseases, hypoplastic anemia, agranulocytosis, etc. On the other hand, an increase in the number of eosinophils is found in such diseases as parasitosis, Hodgkin's disease and allergosis. An increased number of monocytes occurs either during the convalescence period of patients suffering from infectious diseases or in such diseases as monocytic leukemia.

Classification and counting of leukocytes have been made most commonly by the differential counting method which is also referred to as the visual counting method or simply as the manual method. In this method, a blood sample is smeared on a glass slide and the blood corpuscles in the smear are fixed and stained for examination by microscopy. The technician identifies the type of individual leukocytes according to their morphological features (e.g., their size, the morphology of their nucleus and cytoplasm, and the presence or absence of granules) or the degree of dye uptake and performs classification and counting of them. In ordinary laboratories, 100–200 leukocytes are usually counted for each sample and the percentage of the total leukocyte count occupied by each type of corpuscle is recorded as a measured value.

The differential counting method has several disadvantages. First, microscopic observation must be preceded by cumbersome procedures for preparing a specimen that involve such steps as smearing a blood sample on a glass slide, fixing the corpuscles and staining them. Secondly, it is a great burden for the technician to identify subtle differences between corpuscles by microscopic classification and counting. Thirdly, it is difficult even for a skilled technician to yield consistent counts by the manual method since aside from the small number of leukocytes computed, the smeared sample often has an uneven distribution of blood corpuscles.

Various methods have been proposed for eliminating these disadvantages of the manual method of leukocyte classification by achieving automation and such automated techniques may be roughly divided into two types. The first method consists of recording the images of corpuscles with a video camera or some other suitable imaging device and classifying the leukocytes by means of image processing on a computer. The operating principle of this method is similar to that of the conventional visual counting method but primarily due to the existence of many corpuscles that defy classification by processing with a computer, this method has not yet become an ideal alternative to the manual method. Furthermore, this method is not economically feasible since it requires sophisticated equipment which is large and costly.

The other approach toward automatic classification and counting of leukocytes is based on a flow system. In this method, a blood sample having corpuscles suspended in a diluent is permitted to flow in such a way that the corpuscles will individually (one by one) pass through a constricted detector and leukocyte classification is made by analyzing the signal generated by the detector. This second method of leukocyte counting which makes use of a flow system is further subdivided into two categories.

In a method of the first category, an electrolyte in which all red cells that were present have been destroyed with a lysing agent so that only leukocytes will be suspended is permitted to flow through an orifice and the change in electrical impedance that occurs at the orifice when each corpuscle passes through it is detected, with the magnitude of the detected signal being used as a basis for classification of leukocytes.

A method of the second category is characterized by the use of a flow cytometer that comprises a light source, a flow cell that permits the blood cells in a sample to flow one by one through a constricted channel, a photometric unit that detects light issuing from each blood cell, and an analyzer for analyzing the detected signal. In this method, the corpuscles in the sample which are stained are illuminated under light and the fluorescence emitted from the irradiated corpuscles is detected, optionally together with scattered light, with leukocyte classification being made in accordance with the intensity of the detected signal.

Techniques that fall within the category of this flow cytometric method are described in, for example, Japanese Patent Publication No. 853/1984 and L. A. Kamentsky, Blood Cells, 6, 121–140 (1980). According to these techniques, a blood sample is stained with 10 volumes of an Acridine Orange solution, incubated for 1 minute, and irradiated under a light source such as an argon ion laser. The green fluorescence and red fluorescence that are emitted from the individual corpuscles are measured and classification and counting of leukocytes are subsequently made based on a two-dimensional plot of the fluorescence measurements.

Other examples of techniques that are classified as being within the flow cytometric approach are shown in Unexamined Published Japanese Patent Application No. 20820/1975, H. M. Shapiro et al., *J. Histochem. Cytochem.*, 24 (1) 396–411 (1976); and supra, 25 (8) 976–989 (1977). According to these methods, a blood sample is stained with 4 volumes of a Dye Solution I, incubated for 3 minutes, further mixed with 20% formaldehyde in a volume equal to the blood, fixed for 5 minutes, and diluted with a diluting Dye Solution II to obtain a concentration 15–20 times as low as the initial value. The so prepared specimen is subjected to measurement with a flow cytometer.

The flow cytometer employed in these methods uses either a mercury lamp that produces three different wavelengths of light or three lasers, so as to excite the three fluorescent stains in each of the dye solutions. The parameters measured are three kinds of fluorescence, forward scattered light, side-scattered light and absorbed light. Based on these six parameters, two-dimensional plots are constructed in four stages and analyzed to make leukocyte classification and counting.

Unexamined Published Japanese Patent Application No. 70166/1988 discloses a one-step staining process consisting of staining a blood sample with a dye solution comprised of a buffer solution, inorganic salts and fluorescent dyes. But this method has the problem that unlysed erythrocytes may adversely affect measurement data to produce unreliable results.

Unexamined Published Japanese Patent Application No. 134958/1988 discloses a two-step staining process that uses a hypotonic acidic fluorescent dye solution and a solution that will changes its osmolarity and pH. A blood sample stained with those solutions is loaded in a flow cytometer to obtain signals for fluorescence and side-scattered light and on the basis of those signals, a two-dimensional plot of fluorescence intensity vs the intensity of side-scattered light is constructed as shown in FIG. 2, whereby the leukocytes in the sample are classified into five types. Numerals 1–6 in FIG. 2 signify the populations of lymphocytes, monocytes, neutrophils, eosinophils, basophils and a noise component, respectively.

In the first version of the method that uses a flow system for leukocyte classification and counting, the disruption of erythrocytes is a prerequisite but depending on blood sample, it is impossible to effect complete lysis of erythrocytes and the accuracy of measurements may be impaired in such a case.

The examples of the flow cytometric approach that are described in Japanese Patent Publication No. 853/1984 and Blood Cells, 6, 121–140 (1980) are characterized by performing measurements before dye absorption by the cells reaches an equilibrium, or at the time when the difference between the intensities of fluorescence from individual leukocytes attains a maximum during the staining process. However, the time required for attaining an appropriate level of fluorescence intensity in a sample whose leukocyte count is at either one of two extremes will be different from the time for a normal sample and an appropriate staining time must be selected for each sample. As a further problem, this method relies solely on the differential intensity of fluorescence for leukocyte classification and does not necessarily ensure precise separation between different leukocyte types such as lymphocytes and monocytes.

The other examples of the cytometric approach that are described in Unexamined Published Japanese Patent Application No. 20820/1975, J. Histochem, Cytochem., 24 (1) 396–411 (1976) and supra, 25 (8) 976–989 (1977) have the disadvantage that they involve many steps of operation and staining takes a prolonged time and requires the use of reagents in a complex system. Furthermore, practice of these methods requires a very sophisticated and costly apparatus that includes three light sources and which is capable of measuring six parameters. In addition, analysis of such a large number of parameters is inevitably complicated and requires an analyzer having a large capacity.

All of the prior art techniques of flow cytometric approach including the method proposed by Unexamined Published Japanese Patent Application No. 70166/1988 have one common problem in that detection with a flow cytometer is impossible if neutrophils in a blood sample die when a long time passes before measurement. The method described in Unexamined Published Japanese Patent Application No. 134958/1988 aims at detecting dead cells to obtain correct neutrophil counts but, depending on the specimen to be assayed, it is sometimes impossible to achieve complete differentiation of dead cells. The problem also occurs in the case of damaged cells because the zone of their distribution becomes mixed up with the distribution zone of intact cells or another cell type, thereby making it impossible to perform complete differentiation between the two cell groups. In order to avoid these problems, measurements by the conventional flow cytometric methods always require the use of fresh blood samples.

SUMMARY OF THE INVENTION

The present invention has been accomplished under these circumstances and has as an object providing a method capable of more correct classification of leukocytes regardless of the difference between specimens and the presence of cells which, on account of damaged cell membrane or other reasons, are distributed in positions that are different from those which would otherwise occur in a normal situation. The method enables accurate classification and counting of leukocytes by simple procedures.

The method of the present invention for leukocyte classification relies basically upon flow cytometry that uses a first fluid that is hypotonic acidic fluorescent dye solution and a second fluid that is a solution that changes the osmolarity and pH of the first fluid. In accordance with the present invention, a fluorescent dye that specifically stains the nuclei of damaged leukocyte cells is added to the first fluid and the resulting fluid is used in measurements. By analysis conducted on the basis of the resulting two kinds of two-dimensional plot, with them being correlated to each other, the number of leukocyte cells which, on account of a damaged cell membrane or for other reasons, are distributed in positions that are different from those which would otherwise occur in the normal situation, is determined to obtain the final results of leukocyte classification.

Stated more specifically, a third dye such as PI (Propidium iodide) or EB (Ethidium bromide) is added to the first fluid and two kinds of two-dimensional plot, one plotting the intensity of red-fluorescence against the intensity of side-scattered light and the other plotting the intensity of green fluorescence against the intensity of side-scattered light, are analyzed with them being correlated to each other, whereby the number of denatured leukocyte cells, such as neutrophils with damaged cell membranes, that have come to be distributed in different positions than would otherwise be the case in a normal situation on account of such factors as the lapse of a prolonged time after blood sampling can be determined.

The dyes that can be used in the first fluid in accordance with the present invention are listed below:
First dye: Astrazon Yellow 3G
Second dye: Acridine Red;
 Rhodamine S;
 Rhodamine 6G;
 Rhodamine B;
 Rhodamine 19 perchlorate;
 Rhodamine 123;

Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1'-diethyl-9-methylthiocarbocyanine bromide;
2-[γ-(1'-ethyl-4',5'-benzothiazolylidene)-propenyl]-1-ethyl-4,5-benzoxazolium iodide;
Astrazon Red 6B;
C.I. Basic Violet 16;
2-(p-dimethylamlnostyryl)-1-ethyl-4,5-benzothiazolium iodide;
2,4-bis(p-dimethylaminostyryl)-1-ethyl-pyridinium iodide;
2,6-bis(p-dimethylaminostyryl)-1-ethyl-pyridinium iodide;
Astrazon Orange R
Third dye: Propidium iodide;
Etidium bromide;
M-264.

BRIEF DESCRIPTION OF THE DRAWINGS

FIG. 4 is a first type of two-dimensional plot for the intensity of green fluorescence vs the intensity of side-scattered light;

FIG. 5 is a second type of two-dimensional plot for the intensity of red fluorescence vs the intensity of side-scattered light;

DETAILED DESCRIPTION OF THE INVENTION

Figure 1:
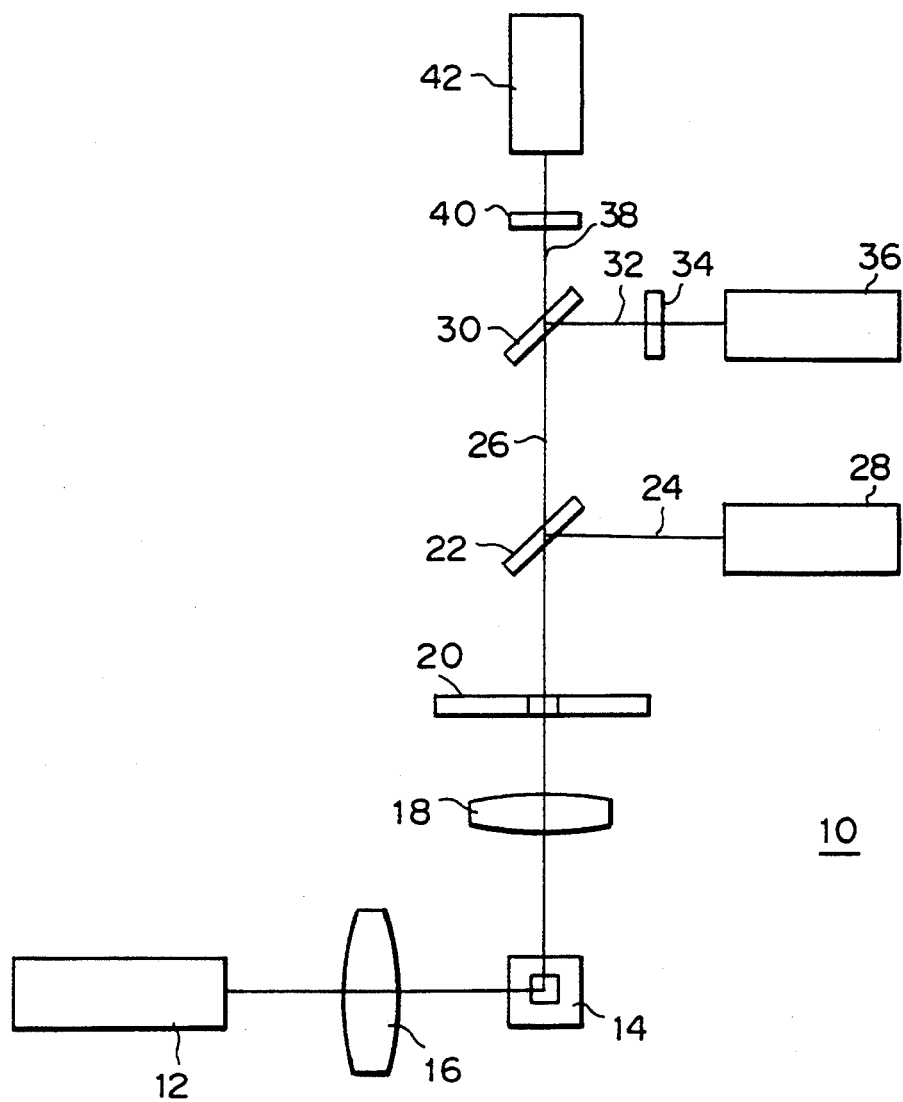
FIG. 1 is a schematic diagram of the optics of a flow cytometer that may be employed in implementing the method of the present invention.

The first and second fluids to be used in the method of the present invention preferably satisfy the following conditions:
(a) Dye concentration Dyes need to be contained in the first fluid at such concentrations that their final concentrations obtained by mixing the first and second fluids will lie within the ranges set forth below.

Basic Yellow 11 and Astrazon Orange R are commercial products that are available from Aldrich Chemical Company, Inc. and Tokyo Kasei K.K., respectively.

If the concentration of Basic Yellow 11 is above a certain level, the intensity of fluorescence from basophils is higher than that from .the other types of leukocytes, and the intensity of fluorescence from eosinophils also increases at higher concentrations. The intensities of fluorescence from lymphocytes, neutrophils and monocytes are virtually independent of the concentration of Basic Yellow 11. Hence, in order to differentiate basophils and eosinophils from the other types of leukocytes in terms of the intensity of fluorescence, the concentration of Basic Yellow 11 may be adjusted to 70–100 ppm and higher.

Separation between noise and the intensity of fluorescence from lymphocytes/neutrophils is possible at Astrazon Orange R concentrations of 100 ppm and above, and good separation can be achieved at concentrations of 200 ppm and above. At concentrations of 300 ppm and above, the efficiency of separation substantially levels off and the intensities of fluorescence from basophils and eosinophils will decrease slightly. Therefore, the concentration of Astrazon Orange R is preferably at 300 ppm or in its neighborhood for achieving efficient separation of leukocytes from noise.

Etidium bromide is a commercial product available from Nacalai Tesque, Inc. If the concentration of Etidium bromide is 3 ppm (3 μg/ml) and below, the appearance of damaged cells in a two-dimensional plot is not consistent (they appear in variable positions). Above 100 ppm, the S/N ratio of signal detection decreases (the difference between a fluorescence signal and the background becomes so small as to prevent effective signal detection). The same discussion may apply to the concentration of Propidium iodide.
(b) pH of the first fluid In order to lyse erythrocytes, the pit of the first fluid is preferably set at 5.0 and below but in order to prevent coagulation of platelets, the pit of the first fluid must be at least 3.5.
(c) Buffer in the first fluid Any buffer that has a pKa value of approximately 4.5, such as citrate, maleate and diglycolate, may be employed in the first fluid. As for diglycolic acid, the intensity of fluorescence from basophils will decrease slightly if the concentration of diglycolic acid is 5 mM and below. On the other hand, the lysing of erythrocytes will be insufficient if the concentration of diglycolic acid is 50 mM and above. An optimum concentration of diglycolic acid is about 10 mM.
(d) Osmolarity of the second fluid There will be no change in the separation pattern even if the final osmolarity of the dye solution is varied from 167 to 387 mOsm/kg by changing the amount of an osmolarity compensating agent (e.g. sodium chloride) added to the second fluid. It is recommended that the osmolarity of the second fluid be adjusted in such a way that the final osmolarity of the dye solution is at an approximately isotonic value (280 mOsm/kg).

(e) Buffer in the second fluid

Any buffer that has a pKa value in an approximate range of 8.5 to 9.0, such as borate, Tris and tricin, may be employed in the second fluid. If tricin is used, the intensity of fluorescence from basophils and eosinophils decreases at a tricin concentration of 50 mM and below. A preferred concentration of tricin is ca. 300 mM.

In accordance with the present invention, not only a fluorescence signal but also a side-scattered light signal is produced from leukocytes. The fluorescence signal reflects the cytochemical characters of leukocytes and depending on the interaction between stains and individual leukocyte types, signals of different intensities are produced from the leukocytes. The right-angle scattering light signal reflects the structural information of an individual white cell. The larger the nucleus of a white blood cell and the more granules that are present in it, the greater the light reflection which will occur in the cell to produce a more intense side-scattered light. A lymphocyte contains very few or no granules, so the scattered light produced from the lymphocyte is the weakest of all leukocytes. On the other hand, a neutrophil contains many granules and has a large nucleus, so it produces a more intense scattered light. Eosinophils produce scattered light the intensity of which is comparable to that produced from neutrophils. Monocytes and basophils produce scattered light having an intensity intermediate between those of scattered light from lymphocytes and neutrophils.

Therefore, as will be described below in detail, by combining a fluorescence signal with a side-scattered light signal, leukocytes can be classified into five types in accordance with the present invention.

A specific example of the optics of a flow cytometer employed in the present invention is hereunder described with reference FIG. 1. The optics shown in FIG. 1 is used in a flow cytometer designed for measuring side-scattered light, red fluorescence and green fluorescence. The optics generally indicated by 10 uses an argon ion laser 12 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated by the laser light, they produce scattered light and fluorescence. The side scattered light and the fluorescence are converged with a condenser lens 18 and pass through an aperture 20 to fall upon a dichroic mirror 22. The dichroic mirror 22 reflects the side scattered light 24 and transmits the fluorescence 26. The side scattered light 24 reflected from the dichroic mirror 22 is detected in a photomultiplier tube 28. Of the two kinds of fluorescence 26 that passes through the dichroic mirror 22, red fluorescence 32 is reflected by a dichroic mirror 30 and green fluorescence 38 is transmitted through that mirror. The reflected red fluorescence 32 passes through a color filter 34 and is detected in a photomultiplier tube 36. The transmitted green fluorescence 38 passes through a color filter 40 and is detected in a photomultiplier tube 42.

Erythrocytes in the blood sample emit only fluorescence of very low intensity, so if all that is needed is to measure the intensity of fluorescence, erythrocytes will not interfere with the counting of leukocytes even if coincidence of erythrocytes and leukocytes occurs (i.e., erythrocytes and leukocytes pass through the detecting portion simultaneously). However, if one wants to measure the scattered light, erythrocytes which produce scattered light having an intensity comparable to that of the scattered light emitted from leukocytes will interfere with the counting of leukocytes. In this case, one may measure fluorescence and scattered light simultaneously and regard as leukocytes only the corpuscles that emit fluorescence having an intensity greater than a certain level. However, if coincidence of leukocytes and erythrocytes occurs, the scattered light from erythrocytes is superposed on the scattered light from leukocytes, thereby making accurate measurement of scattered light from the leukocytes impossible. In the optics 10 of a flow cytometer shown in FIG. 1, a blood sample is permitted to flow through the flow cell 14 after it has been diluted by, for example, 20 fold so that the probability of coincidence of erythrocytes and leukocytes is reduced and the potential interference by erythrocytes is decreased to a level that can be disregarded for practical purposes.

Specifically, the method of the present invention is an improvement of the invention described in Unexamined Published Japanese Patent Application No. 282698/1988 (Example 2, 2: 2-step method) and it is illustrated below with reference to a working example. It should, however, be noted that the following example is in no way intended to limit the present invention.

EXAMPLE

Two reagents were prepared to the formulas indicated below. The first dye in the first fluid was a fluorescent dye that would selectively stain both eosinophils and basophils; the second dye in the first fluid was a fluorescent dye that would stain the nuclei of leukocytes; and the third dye in the first fluid was a fluorescent dye that would stain the nuclei of leukocytes that were damaged in a cell membrane.

| First fluid | | |
| --- | --- | --- |
| First dye | Basic Yellow 11 (Aldrich) | 100 ppm |
| Second dye | Astrazon Orange R (Tokyo Kasei) | 330 ppm |
| Buffer | Diglycolic acid-sodium hydroxide | 10 mM |
| Third dye | Etidium bromide | 5.5 ppm (preferably 3–100 ppm) |
| pH, 4.0; osmolarity, 30 mOsm/kg | | |

In the first fluid, EB (Etidium bromide) would bind to a G-C pair in DNA by intercalation and so would PI (Propidium iodide).

| Second fluid | | |
| --- | --- | --- |
| Buffer | Tricin-sodium hydroxide | 300 mM |
| Osmolarity adjusting agent | Sodium chloride | 750 mM |
| pH, 9.8–9.9; osmolarity, 2200 mOsm/kg | | |

Using the thus prepared first and second fluids, fluorescence and scattered light were measured for leukocyte classification in the following manner.

First, the blood of a healthy person was made non-clotting and 100 μl of the thus anti-coagulated blood was mixed uniformly with 1800 μl of the first fluid. After agitation, the mixture was incubated at 25° C. for ca. 20 seconds. Thereafter, 200 μl of the second fluid was added and the mixture was agitated, followed by incubation at 25° C. for ca. 40 seconds. The finally obtained sample solution had a pit of 8.6–8.7 and an osmolarity of ca. 280 mOsm/kg (isotonic).

In this way, sample solutions were prepared with the erythrocytes lysed and the various types of leukocytes stained. Those sample solutions were loaded in a flow cytometer for measuring the intensities of fluorescence and scattered light from the leukocytes.

The results of measurements are described below with reference to the accompanying FIGS. 2–13.

Figure 2:
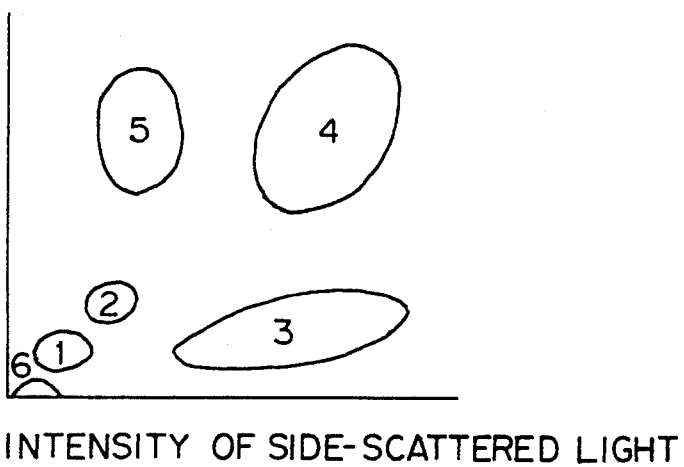
FIG. 2 is a two-dimensional plot for the intensity of green fluorescence vs the intensity of side-scattered light, as obtained in measurement of a fresh blood sample (within 6 h after sampling) using a prior art reagent, i.e., the first fluid in the absence of the third dye.

FIG. 2 is a two-dimensional plot of the intensity of green fluorescence vs the intensity of side-scattered light as obtained when measurements were conducted using the prior art reagent, namely the first fluid not containing the third dye. Numerals 1–6 in the plot signify the distribution zones of lymphocytes, monocytes, neutrophils, eosinophils, basophils and erythrocyte ghost, respectively. (A two-dimensional plot of the intensity of red fluorescence vs the intensity of side-scattered light was found to show the same pattern of distribution.) By separating each distribution zone and counting the number of particles in it, the count of leukocytes of a specific type can be obtained. By repeating this procedure, the proportions of different types of leukocytes can be determined.

Figure 3:
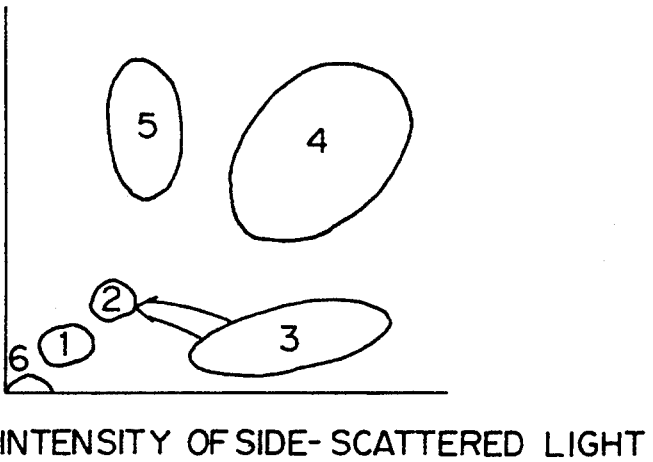
FIG. 3 is a two-dimensional plot for the intensity of green fluorescence vs the intensity of side-scattered light, as obtained in the same measurement except that the blood sample was left at room temperature for a prolonged period, say for 20 h.

The two-dimensional plot of FIG. 2 shows the results of measurements on fresh blood that was not left to stand for more than 6 hours after sampling. If sampled blood is left at room temperature for a prolonged time, say 20 hours, before measurement, the cell membranes of leukocytes are damaged and some of them will be distributed in a different zone than the cells of interest would otherwise be located. If the distribution of such cells is within the zone of another type of cells, the precision of leukocyte classification will decrease. The effect of overlap between two distribution zones is the greatest if, as shown in FIG. 3, some part of the neutrophil population is distributed in the zone of monocytes. When the conventional reagent was used, the two kinds of two-dimensional plot (one for plotting the intensity of green fluorescence vs the intensity of side-scattered light and the other for plotting the intensity of red fluorescence vs the intensity of side-scattered light). Hence, in the conventional practice, a certain zone is set in each two-dimensional plot as an area where substantially no leukocytes are distributed if the blood is fresh but where a measurable number of leukocytes appear if the blood is left to stand for a prolonged time, and the cells falling in that zone have been regarded as dead neutrophil cells.

However, this approach has not always assured satisfactory precision on account of various factors such as variations among specimens and the difference in the degree of cell damage.

Figure 12:
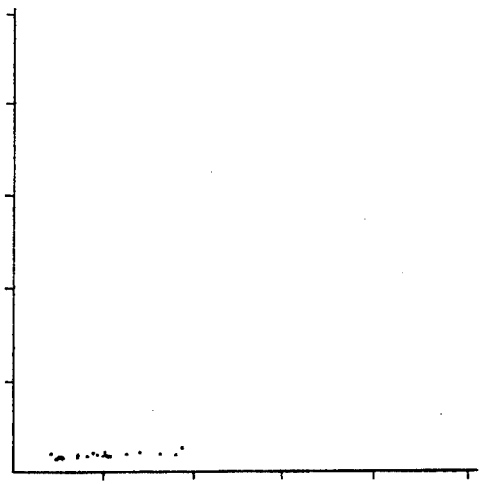
FIG. 12 is another two-dimensional plot of the intensity of green fluorescence vs the intensity of side-scattered light.
Figure 13:
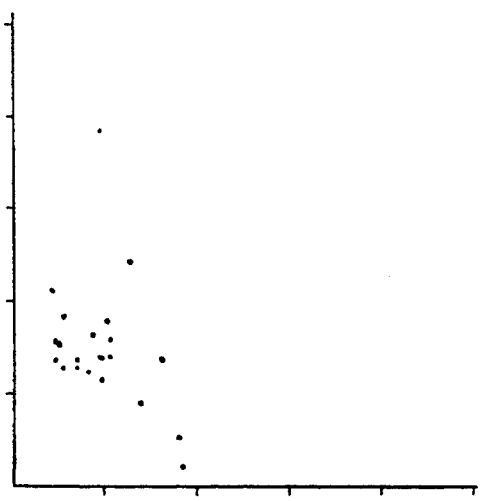
FIG. 13 is another two-dimensional plot of the intensity of red fluorescence vs the intensity of side-scattered light.

Under these circumstances, the method of the present invention modifies the conventional reagent and uses the first fluid incorporating the third dye and this has proved to be very effective in maintaining the precision of leukocyte classification at high level. Etidium bromide used in the example under consideration is known as a substance that stains dead cells. However, when measurements were conducted using a fluid that did not contain the first or second dye but which contained Etidium bromide as the sole dye (the other conditions of preparation were the same as described above), damaged cells could not be detected even from blood samples that contained many damaged leukocyte cells. This fact is clear from FIGS. 12 and 13. FIG. 12 is a two-dimensional plot of the intensity of green fluorescence vs the intensity of side-scattered light, and FIG. 13 is a two-dimensional plot of the intensity of red fluorescence vs the intensity of side-scattered light. Obviously, damaged leukocyte cells were not detectable in either case.

Figure 10:
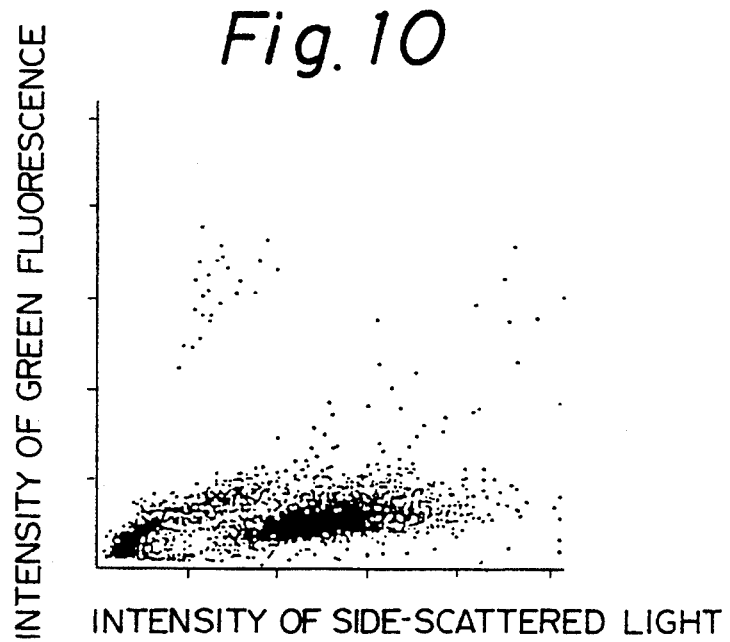
FIG. 10 is a two-dimensional plot of the intensity of green fluorescence vs the intensity of side-scattered light.
Figure 11:
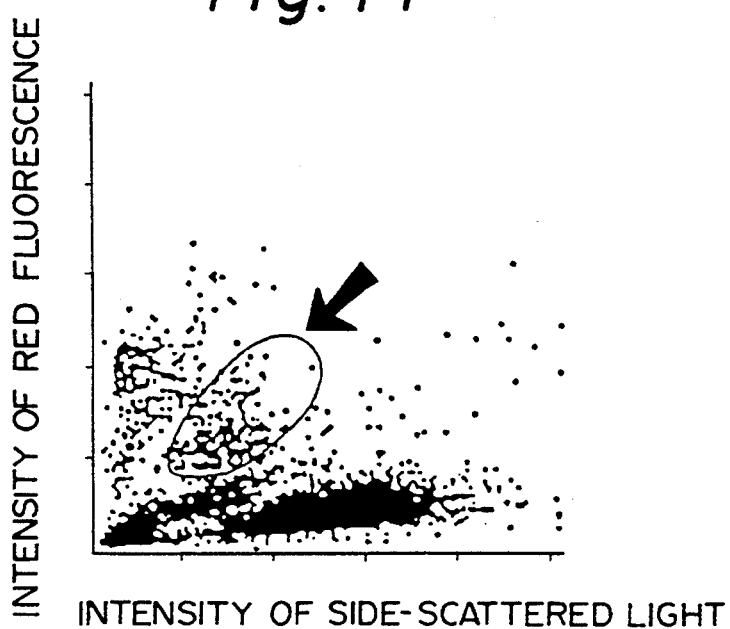
FIG. 11 is a two-dimensional plot of-the intensity of red fluorescence vs the intensity of side-scattered light.

When measurements were conducted on the same specimens using the first fluid under consideration which incorporated not only the third dye but also the first and second dyes, damaged leukocyte cells could be detected as distinct entities from the intact cells. FIGS. 10 and 11 are two-dimensional plots; the graph of FIG. 10 plots the intensity of green fluorescence vs the intensity of side-scattered light and the graph of FIG. 11 plots the intensity of red fluorescence vs the intensity of side-scattered light. The damaged leukocyte cells are shown in FIG. 11 as enclosed with a circle. In short, it is of great importance to incorporate not only the first and second dyes but also the third dye in the reagent for leukocyte classification and the present invention has been accomplished on the basis of the finding of this important fact.

The distribution zones of various leukocyte types that can be obtained by the method of the present invention using the first fluid described above are discussed more specifically below.

FIG. 5 is a second two-dimensional plot of the intensity of red fluorescence vs the intensity of side-scattered light. Numerals 1–8 in the plot signify the zones of lymphocytes, monocytes, neutrophils, eosinophils, basophils, erythrocyte ghost, neutrophils with damaged cell membrane, and lymphocytes with damaged cell membrane, respectively. FIG. 4 is a first two-dimensional plot of the intensity of green fluorescence vs the intensity of side-scattered light. The distribution pattern appearing in FIG. 4 is substantially the same as that obtained using the conventional first fluid; the zone of lymphocytes 8 with damaged cell membrane is within the zone of intact lymphocytes 1 whereas the zone of neutrophils 7 with damaged cell membrane is within the zone of monocytes 2. It should also be noted that the first two-dimensional plot (FIG. 4) has a different distribution pattern from the second two-dimensional plot (FIG. 5). Precise leukocyte classification can be accomplished by performing analysis with the two plots being correlated to each other.

The specific method of data analysis is described below. Those distribution zones in the first two-dimensional plot which are clearly distinguished from one another are separated as such. As for the zones that are not clearly discernible from others, the second two-dimensional plot is constructed to perform more precise separation.

Figure 6:
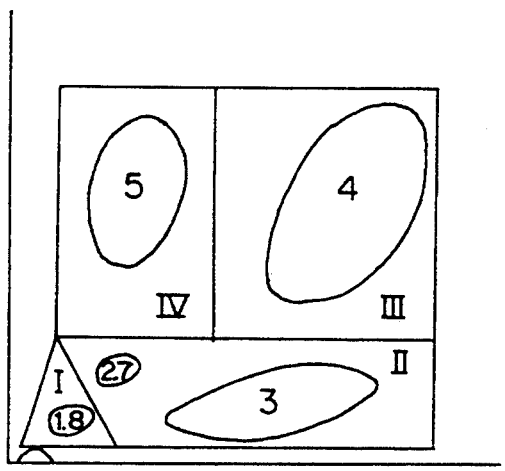
FIG. 6 is a two-dimensional plot obtained by fractionating the first type of two-dimensional plot shown in FIG. 4.

To begin with, the first two-dimensional plot (FIG. 4) is fractionated as shown in FIG. 6; zone I covers both intact lymphocytes 1 and damaged lymphocytes 8; zone II covers monocytes 2, intact neutrophils 3 and damaged neutrophils 7; zone III covers eosinophils 4; and zone IV covers basophils 5.

Figure 7:
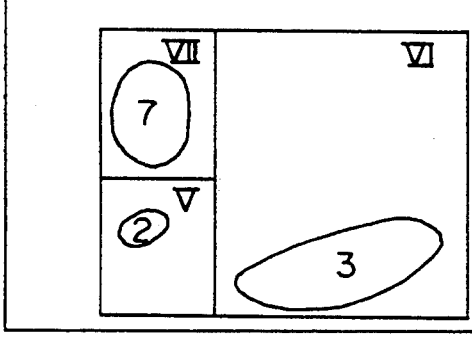
FIG. 7 is a second type of two-dimensional plot as constructed for the three cell types within zone II of FIG. 6.

In the next step, the second two-dimensional plot (see FIG. 7) is constructed for the three types of cells in zone II that are not clearly distinguishable from one another. Those three types of cells do not provide distinct distributions in the first two-dimensional plot but they do provide distinct distributions in the second two-dimensional plot. This is why the three types of cells in zone II are subjected to further separation as shown in FIG. 7, in which zone V covers monocytes 2, zone VI covers intact neutrophils 3, and zone VII covers damaged neutrophils 7. Combining the cells in zones VI and VII, the total count of neutrophils is obtained.

Thus, the counts of all leukocyte types of interest can be determined with high precision.

The consistency of leukocyte classification by the method of the present invention is described below.

Figure 8:
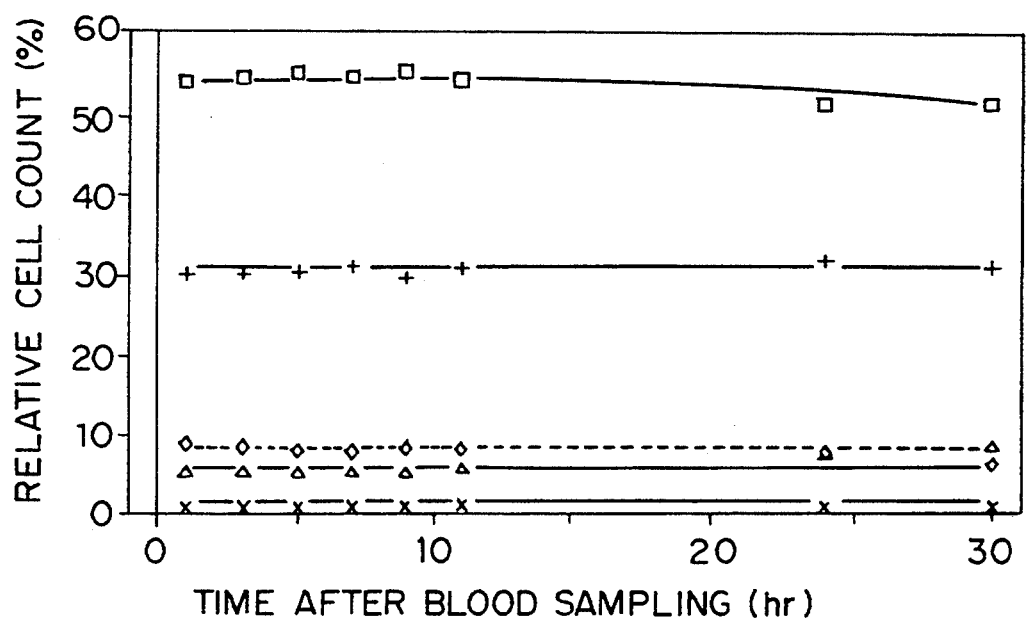
FIG. 8 is a graph showing the time-dependent profiles of the relative counts of five leukocyte types as obtained by performing analysis with the first and second fluids used in the example to be described below.

FIG. 8 is a graph showing the time-dependent profiles of the relative counts of five leukocyte types as obtained by performing analysis with the first and second fluids used in the example under discussion. The horizontal axis plots the time (in hours) for which blood was left to stand at room temperature after sampling. The symbols in the graph have the following meanings: □, neutrophils; +, lymphocytes; ◇, monocytes; △, eosinophils; and ×, basophils.

As FIG. 8 shows, the proportions of the five leukocyte counts remained stable for more than 20 hours after sampling.

Figure 9:
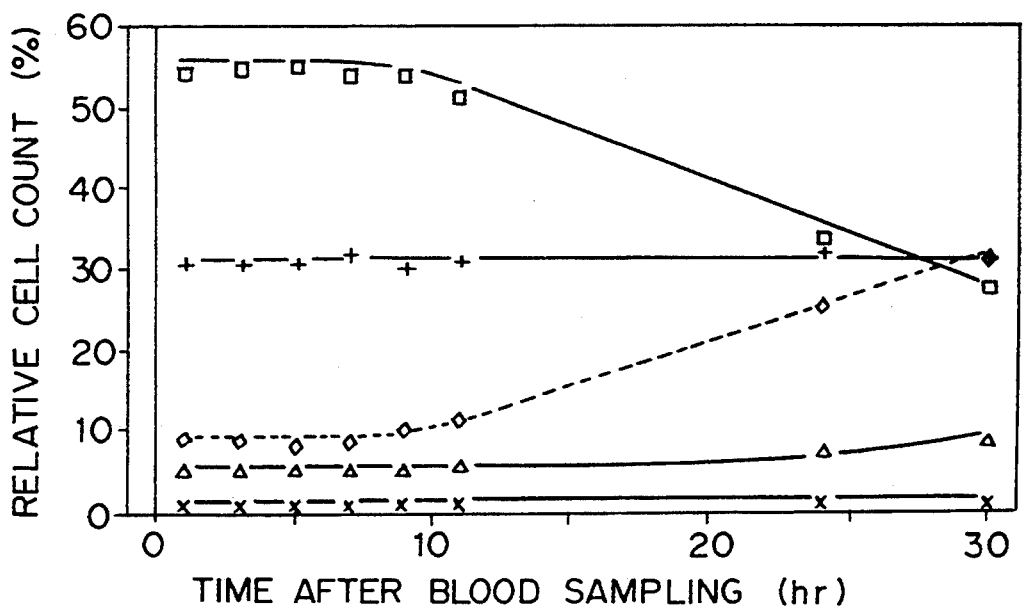
FIG. 9 is a graph showing the results of leukocyte classification that was performed with the prior art first fluid, followed by analysis on the basis of a two-dimensional plot of the intensity of green fluorescence vs the intensity of side-scattered light.

FIG. 9 is a graph showing the results of leukocyte classification that was performed with the prior art first fluid, followed by analysis on the basis of the resulting two-dimensional plot of the intensity of green fluorescence vs the intensity of side-scattered light. Obviously, the proportion of neutrophils started to decrease and that of monocytes started to increase with the lapse of ca. 8 h after sampling.

In the example under discussion, Etidium bromide was used as the third dye but Propidium iodide and M-264 can also be used with equal effectiveness.

The first fluid to be used in the method of the present invention incorporates not only the first and second dyes but also the third dye and this insures that even leukocytes with a damaged cell membrane can be distributed as entities distinct from other leukocyte types on a two-dimensional plot. Hence, such damaged leukocyte cells can be detected in a consistent manner irrespective of the differences between specimens and those in the degree of cell damage. In accordance with the present invention, final results of measurements are produced by analyzing the detected data and, hence, high precision of leukocyte classification is assured even in the case of assaying blood that contains damaged cells as a result of prolonged standing at room temperature after sampling.

What is claimed is:

1. A method of classifying leukocytes by flow cytometry which comprises the steps of:
    (a) mixing a sample of blood with hypotonic first fluid comprising a first dye that is a fluorescent dye capable of selectively staining both eosinophils and basophils, said first dye being Astrazon Yellow 3G, a second dye that is a fluorescent dye capable of staining the nuclei of leukocytes, said second dye selected from the group consisting of:
    Acridine Red;
    Rhodamine S;
    Rhodamine 6G
    Rhodamine B
    Rhodamine 19 perchlorate;
    Rhodamine 123
    Eosin Y;
    Cyanosine;
    Cresyl Fast Violet;
    Darrow Red;
    Acronol Phloxine FFS;
    1,1'-dimethylthiocarbocyanine;
    1,1'-diethylthiocarbocyanine;
    1,1-diethyl-9-methylthiocarbocyanine bromide;
    2-[γ-(1'-ethyl-4', 5'-benzothiazolylidene) -propenyl]-1-ethyl-4,5-benzoxazolium iodide;
    Astrazon Red 6B;
    Basic Violet 16;
    2-(p-dimethylaminostyryl-1-ethyl-4,5 benzothiazolium iodide;
    2,4-bis(p-dimethylaminostyryl)-1-ethyl-pyridinium iodide;
    2,6-bis(p-dimethylaminostyryl)-1-ethyl-pyridinium iodide; and
    Astrazon Orange R;
    a third dye that is a fluorescent dye capable of staining the nuclei of leukocytes with damaged cell membrane, said third dye selected from the group consisting of Propidium Iodide, Etidium Bromide and M-264, and a buffer for maintaining a pH in an acidic range to obtain a first sample solution, incubating said first sample solution;
    (b) mixing the first sample solution obtained in step (a) with a second fluid comprising a buffer that neutralizes acid in the first fluid for maintaining the pH of the solution at a staining pH and an osmolarity adjusting agent for adjusting the osmolarity of the solution to a value at which the leukocytes remain unchanged in shape to obtain a second sample solution, incubating said second sample solution, said dyes cooperating to enable a combined total incubation period of about one minute;
    (c) loading the second sample solution obtained in step (b) in a flow cytometer and obtaining more than one signal for parameters including fluorescence and scattered light in association with individual types of leukocytes;
    (d) constructing a first two-dimensional plot of intensities of scattered light and green fluorescence from the signals as emitted from leukocytes, said plot containing distribution zones of each intact leukocyte type, and counting leukocytes within each zone to obtain a number for each leukocyte type located in the distribution zones of intact leukocytes;
    (e) further separating and counting leukocytes within distribution zones of individual leukocyte types on said first two-dimensional plot by determining distribution zones for leukocytes that deviate from the distribution zones of intact leukocytes where they would otherwise be located,
    (f) Constructing, for the leukocyte groups in those determined distribution zones that deviate from the distribution zones of intact leukocytes, a second two-dimensional plot of the intensities of scattered light and red fluorescence,
    (g) separating on said second two-dimensional plot those leukocytes that deviate and counting to obtain a number of such leukocytes in each zone;
    (h) combining the number of each leukocyte type located in the distribution zones of intact leukocytes and the number of leukocytes that deviate from said zones to obtain a total number of each type of leukocytes in said blood sample.

2. A method according to claim 1 wherein the individual types of leukocytes are comprised of monocytes and neutrophils, and the distribution zones set in the first two-dimensional plot are the distribution zones of monocytes and neutrophils and, monocytes, intact neutrophils, and neutrophils with damaged cell membranes are separated from one another on the second two-dimensional plot.

3. A method of classifying leukocytes by flow cytometry which comprises the steps of:
(a) mixing a sample of blood with a hypotonic first fluid comprising a first dye that is a fluorescent dye capable of selectively staining both eosinophils and basophils, said first dye being Astrazon Yellow 3G, a second dye that is a fluorescent dye capable of staining the nuclei of leukocytes, said second dye selected from the group consisting of:
Acridine Red;
Rhodamine S;
Rhodamine 6G
Rhodamine B
Rhodamine 19 perchlorate;
Rhodamine 123
Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1-diethyl-9-methylthiocarbocyanine bromide;
2-[γ-(1'-ethyl-4', 5'-benzothiazolylidene) -propenyl]-1-ethyl-4,5-benzoxazolium iodide;
Astrazon Red 6B;
Basic Violet 16;
2-(p-dimethylaminostyryl-1-ethyl-4,5 benzothiazolium iodide;
2,4-bis(p-dimethylaminostyryl)-1-ethyl-pyridinium iodide;
2,6-bis(p-dimethylaminostyryl)-1-ethyl-pyridinium iodide; and
Astrazon Orange R;
a third dye that is a fluorescent dye capable of staining the nuclei of leukocytes with damaged cell membrane, said third dye selects from the group consisting of Propidium Iodide Etidium Bromide and M-264, and a buffer for maintaining a pH in an acidic range to obtain first sample solution, incubating said first sample solution;
(b) mixing the first sample solution obtained in step (a) with a second fluid comprising a buffer that neutralizes acid in the first fluid for maintaining the pH of the solution at a staining pH and an osmolarity adjusting agent for adjusting the osmolarity of the solution a value at which the leukocytes remain unchanged in shape to obtain a second sample solution, incubating said second sample solution, said dyes cooperating to enable a combined total incubation period of about one minute;
(c) loading the second sample solution obtained in step (b) in a flow cytometer and obtaining more than one signal for parameters including fluorescence and scattered light in association with individual types of leukocytes;
(d) constructing a first two-dimensional plot of intensities of scattered light and green fluorescence from the signals as emitted from leukocytes, said plot containing distribution zones of each leukocyte type, and counting leukocytes within each zone to obtain a number for undamaged leukocytes of each leukocyte type located in the distribution zones of intact leukocytes;
(e) further separating and counting leukocytes within distribution zones of individual leukocyte types on said first two-dimensional plot by determining distribution zones for leukocytes with damaged membranes,
(f) constructing, for the leukocytes with damaged membranes in those determined distribution zones for leukocytes with damaged membranes, a second two-dimensional plot of the intensities of scattered light and red fluorescence,
(g) separating on said second two-dimensional plot those leukocytes with damaged membrane and counting to obtain a number for damaged leukocytes of each leukocyte type located in the zones of leukocytes with damaged membranes;
(h) combining the number of undamaged leukocytes located in the zones of intact leukocytes and the number of damaged leukocytes located in the zones of leukocytes with damaged membranes to obtain a total number of each type of leukocytes in said blood sample.

4. A method of classifying leukocytes by flow cytometry which comprises the steps of:
(a) mixing a sample of blood with a hypotonic first fluid comprising a first dye that is a fluorescent dye capable of selectively staining both eosinophils and basophils, said first dye being Astrazon Yellow 3G a second dye that is a fluorescent dye capable of staining the nuclei of leukocytes, said second dye selected from the group consisting of:
Acridine Red;
Rhodamine S;
Rhodamine 6G
Rhodamine B
Rhodamine 19 perchlorate;
Rhodamine 123
Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1-diethyl-9-methylthiocarbocyanine bromide;
2-[γ-(1'-ethyl-4', 5'-benzothiazolylidene) -propenyl]-1-ethyl-4,5-benzoxazolium iodide;
Astrazon Red 6B;
Basic Violet 16;
2-(p-dimethylaminostyryl-1-ethyl-4,5 benzothiazolium iodide;
2,4-bis(p-dimethylaminostyryl)-1-ethyl-pyridinium iodide;
2,6-bis(p-dimethylaminostyryl)-1-ethyl-pyridinium iodide; and
Astrazon Orange R;
a third dye that is a fluorescent dye capable of staining the nuclei of leukocytes with damaged cell membrane, said third dye selected from the group consisting of Propidium Iodide, Etidium Bromide and M-264, and a buffer for maintaining a pH in an acidic range to obtain a first sample solution, incubating said first sample solution;

(b) mixing the first sample solution obtained in step (a) with a second fluid comprising a buffer that neutralizes acid in the first fluid for maintaining the pH of the solution at a staining pH and an osmolarity adjusting agent for adjusting the osmolarity of the solution to a value at which the leukocytes remain unchanged in shape to obtain a second sample solution, incubating said second sample solution, said dyes cooperating to enable a combined total incubation period of about one minute;

(c) loading the second sample solution obtained in step (b) in a flow cytometer and obtaining more than one signal for parameters including fluorescence and scattered light in association with individual types of leukocytes;

(d) constructing a first two-dimensional plot of intensity of scattered light plotted against intensity of green fluorescence from the respective signals as emitted from leukocytes in said flow cytometer, said plot defining distribution zones of each intact leukocyte type, and counting to obtain a number for each leukocyte type located in the distribution zones of intact leukocytes;

(e) further separating leukocyte cell groups within each distribution zone, by constructing for each distribution zone a second plot of the intensity of scattered light plotted against intensity of red fluorescence from the respective signals emitted from leukocytes in said flow cytometer, whereby said second plot includes cells having damaged membrane of leukocyte types that would be found in distribution zones for each intact leukocyte type.

(f) distinguishing on said second plot said leukocyte cell groups having damaged membranes, and counting to obtain a number for each type of leukocyte having damaged membranes in each distribution zone; and (g) combining the number for each leukocyte type located in the distribution zones of intact leukocytes and the number of for each type of leukocyte having damaged membranes to obtain a total number of each type of leukocytes in said blood sample.

5. A method according to claim 3 wherein the distribution zones set in the first two-dimensional plot are the distribution zones of monocytes and neutrophils and, monocytes, intact neutrophils and neutrophils with damaged cell membrane are separated from one another on the second two-dimensional plot.

6. A method according to claim 4 wherein the distribution zones set in the first two-dimensional plot are the distribution zones of monocytes and neutrophils and, monocytes, intact neutrophils and neutrophils with damaged cell membrane are separated from one another on the second two-dimensional plot.

7. The method as defined in claims 1, 3, or 4, wherein said step of loading the second sample and obtaining signals includes irradiating said second sample with a single wavelength.

8. The method as defined in claim 7, wherein said single wavelength is 488 nm.

9. The method as defined in claims 1 or 3 comprising the additional step preceding step (b) of:
incubating said first sample for a period of time equal to less than 1 minute.

10. The method as defined in claim 9, comprising the additional step preceding step (c) of:
incubating said second sample for a period of time equal to less than 1 minute.

11. The method as defined in claim 10, wherein said incubation time of said first sample combined with said incubation time of said second sample is less than 1 minute.

* * * * *

UNITED STATES PATENT AND TRADEMARK OFFICE
CERTIFICATE OF CORRECTION

PATENT NO.   : 5,434,081
DATED        : July 18, 1995
INVENTOR(S)  : Yasunori Maekawa It is certified that error appears in the above-indentified patent and that said Letters Patent is hereby corrected as shown below:

On the title page, item [73] Assignee: should read

--TOA Medical Electronics Co., Ltd., Japan--.

Signed and Sealed this

Sixteenth Day of April, 1996

BRUCE LEHMAN

*Attest:*

*Attesting Officer*  *Commissioner of Patents and Trademarks*